United States Patent [19]

Claremon et al.

[11] Patent Number: 5,441,952

[45] Date of Patent: Aug. 15, 1995

[54] FIBRINOGEN RECEPTOR ANTAGONISTS

[75] Inventors: David A. Claremon, Maple Glen; Nigel Liverton, Harleysville, both of Pa.

[73] Assignee: Merck & Co., Inc., Rahway, N.J.

[21] Appl. No.: 42,963

[22] Filed: Apr. 5, 1993

[51] Int. Cl.⁶ .................... C07D 211/62; A61K 38/00
[52] U.S. Cl. ...................................... 514/221; 540/500
[58] Field of Search .......................... 540/500; 514/221

[56] References Cited

U.S. PATENT DOCUMENTS

| | | | |
|---|---|---|---|
| 4,122,255 | 10/1980 | Krapcho | 542/421 |
| 4,243,807 | 1/1981 | Frieb et al. | 546/232 |
| 4,313,947 | 2/1982 | Nakagawa et al. | 424/248.54 |
| 4,622,331 | 11/1986 | Jozie | 514/331 |
| 5,030,654 | 7/1991 | Barnish | 514/510 |

FOREIGN PATENT DOCUMENTS

| | | |
|---|---|---|
| 0229391 | 12/1986 | European Pat. Off. . |
| 0372486 | 12/1989 | European Pat. Off. . |
| 0352249 | 1/1990 | European Pat. Off. . |
| 0381033 | 1/1990 | European Pat. Off. . |
| 0384362 | 2/1990 | European Pat. Off. . |
| 0405537 | 6/1990 | European Pat. Off. . |

OTHER PUBLICATIONS

CA 74: 22903 (Schmidt), German Offen 1923821 70/11/19, 1970.)

*Primary Examiner*—Johann Richter
*Assistant Examiner*—Catherine S. Kilby Scalzo
*Attorney, Agent, or Firm*—Richard S. Parr; Melvin Winokur

[57] ABSTRACT

Fibrinogen receptor antagonists of the

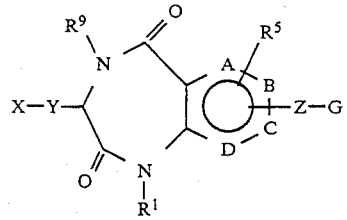

are disclosed for use in inhibiting the binding of fibrinogen to blood platelets and for inhibiting the aggregation of blood platelets, for example

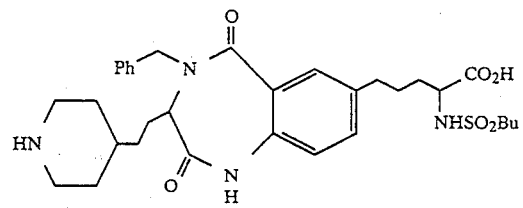

22 Claims, No Drawings

FIBRINOGEN RECEPTOR ANTAGONISTS

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood. The general formula for the peptides includes an Arg-Gly-Asp sequence.

Tjoeng et al., EP 352,249, describe platelet aggregation inhibitors which antagonize interactions between fibrinogen and/or extracellular matrix proteins and the platelet gpIIb/IIIa receptor, including 8-guanido-octanoyl-Asp-2-(4-methoxyphenyl)ethyl amide.

Alig et al., EP 372,486, describe N-aryl beta-amino acids which inhibit fibrinogen, fibronectin and von Willebrand factor to the blood platelet fibrinogen receptor (glycoprotein IIb/IIIa).

Alig et al., EP 381,033, describe di-aryl or heteroaryl substituted alkanoic acid derivatives of a defined formula which inhibit binding of proteins to their specific receptors on cell surfaces, including fibrinogen.

Alig et al., EP 384,362, describe glycine peptides of a specified formula containing an amidine group which inhibit binding of fibrinogen to platelet fibrinogen receptors.

Horwell et al., EP 405,537, describe N-substituted cycloalkyl and polycycloalkyl alpha-substituted Trp-Phe- and phenethylamine derivatives which are useful for treating obesity, hypersecretion of gastric acid in the gut, gastrin-dependent tumors, or as antipsychotics.

It is an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

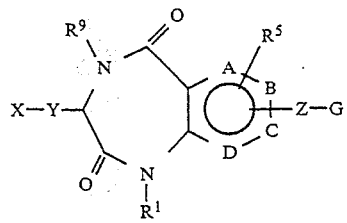

wherein G is

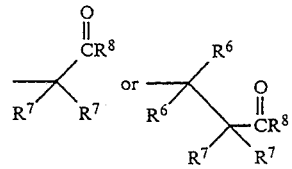

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

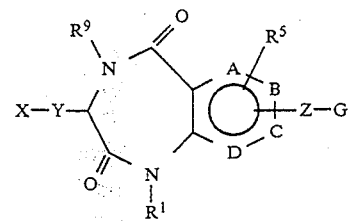

wherein G is

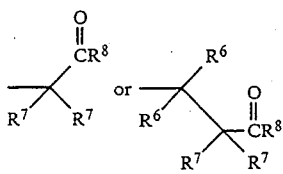

A, B, C and D independently represent a carbon atom or a nitrogen atom;
X is

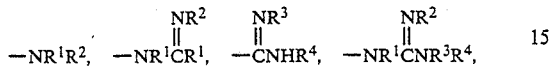

or a 4- to 10- membered mono- or polycyclic aromatic or nonaromatic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen,
$C_{1-10}$ alkyl,
aryl $C_{0-8}$ alkyl,
oxo,
thio,
amino $C_{0-8}$ alkyl, $C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkoxy $C_{0-6}$ alkyl,
carboxy $C_{0-6}$ alkyl, $C_{1-3}$ alkoxycarbonyl $C_{0-6}$ alkyl,
carboxy $C_{0-6}$ alkyloxy,
hydroxy $C_{0-6}$ alkyl, and
fused or nonfused heteroaryl $C_{0-8}$ alkyl, wherein the heteroaryl group contains 1, 2, 3 or 4 heteroatoms N, O, or S;
Y is
$C_{0-8}$ alkyl,
$C_{0-8}$ alkyl-$NR^3$-CO-$C_{0-8}$ alkyl,
$C_{0-8}$ alkyl-$CONR^3$-$C_{0-8}$ alkyl,
$C_{0-8}$ alkyl-O-$C_{0-8}$ alkyl,
$C_{0-8}$ alkyl-$S(O_n)$-$C_{0-8}$ alkyl, or
$C_{0-8}$ alkyl-$SO_2$-$NR^3$-$C_{0-8}$ alkyl-,
$C_{0-8}$ alkyl-$NR^3$-$SO_2$-$C_{0-8}$ alkyl-, or
$C_{1-8}$ alkyl-CO-$C_{0-8}$ alkyl;
Z is
—$(CH_2)_m$—, —C≡C—$CH_2$— or

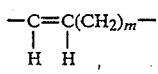

wherein m is 0–6;
$R^5$ is
hydrogen
$C_{1-6}$ alkyl,
$C_{0-6}$ alkylcarboxy $C_{0-6}$ alkyl,
$C_{0-6}$ alkyloxy $C_{0-6}$ alkyl,
hydroxy $C_{0-6}$ alkyl,
aryl $C_{0-6}$ alkyl, or
halogen;
$R^6$ is
hydrogen,
$C_{1-8}$ alkyl,
aryl $C_{0-6}$ alkyl,
$C_{3-8}$ cycloalkyl $C_{0-6}$ alkyl,
$C_{0-6}$ alkylcarboxy $C_{0-6}$ alkyl, carboxy $C_{0-6}$ alkyl,
$C_{1-4}$ alkyloxy $C_{0-6}$ alkyl, or
hydroxy $C_{0-6}$ alkyl, provided that any of which groups may be substituted or unsubstituted independently with $R^1$ or $R^2$, and provided that, when two $R^6$ groups are attached to the same carbon, they may be the same or different;
$R^7$ is
hydrogen, fluorine
$C_{1-8}$ alkyl,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ -alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl
aryl $C_{0-6}$ alkylcarbonyl $C_{0-6}$ alkyl,
$C_{1-6}$ alkylthiocarbonylamino $C_{0-6}$ alkyl, or
aryl $C_{0-6}$ alkylthiocarbonylamino $C_{0-6}$ alkyl
wherein groups may be unsubstituted or substituted with one or more substituents selected from $R^1$ and $R^2$, and provided that when two $R^7$ groups are attached to the same carbon atom, they may be the same or different;
$R^8$ is
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy, or
an L- or D-amino acid joined by an amide linkage and wherein the carboxylic acid moiety of said amino acid is as the free acid or is esterified by $C_{1-6}$ alkyl; and
$R^9$ is
hydrogen, $C_{1-8}$ alkyl, or -W -V, wherein W is $C_{1-3}$ alkyl and V is 5- to 7-membered monocyclic aromatic or nonaromatic ring system containing 0, 1, 2, 3 or 4 heteroatoms selected from N, O and S.

When substituent $R^1$, $R^2$, $R^3$, $R^4$, $R^5$, $R^6$, $R^7$, $R^8$ or Y includes the definition $C_0$, (e.g. aryl $C_0$ alkyl), the group modified by $C_0$ is not present in the substituent.

"Aryl" means a mono- or polycyclic system composed of 5- and 6- membered aromatic rings containing 0, 1, 2, 3 or 4 heteroatoms chosen from N, O or S and either unsubstituted or substituted with $R^1$.

"Alkyl" means straight or branched chain alkane, alkene or alkyne.

"Halogen" includes fluorine, chlorine, iodine and bromine.

A preferred embodiment of the present invention is

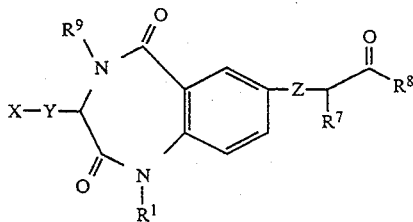

wherein
X is
—NR$^1$R$^2$ or a 4- to 10-membered mono- or polycyclic aromatic or non-aromatic ring system containing 0, 1 or 2 heteroatoms chosen from N or O and either unsubstituted or substituted with R$^1$ and R$^2$, wherein R$^1$ and R$^2$ are independently chosen from:
  hydrogen,
  C$_{1-6}$ alkyl,
  aryl C$_{0-6}$ alkyl,
  carboxy C$_{0-6}$ alkyl,
  hydroxy C$_{0-6}$ alkyl,
  C$_{1-3}$ alkyloxy C$_{0-6}$ alkyl, or
  amino C$_{0-6}$ alkyl;
Y is
  C$_{0-6}$ alkyl,
  C$_{1-6}$ alkyl-CO-C$_{0-6}$ alkyl, or
  C$_{0-6}$ alkyl-NR$^3$-CO-C$_{0-6}$ alkyl, wherein R$^3$ is hydrogen,
  C$_{1-6}$ alkyl,
  aryl C$_{0-6}$ alkyl,
  carboxy C$_{0-6}$ alkyl,
  hydroxy C$_{0-6}$ alkyl,
  C$_{1-3}$ alkyloxy C$_{0-6}$ alkyl, or
  amino C$_{0-6}$ alkyl;
Z is
  —(CH$_2$)$_m$—, or —C≡C—CH$_2$—;
  wherein m is 0–6;
R$^3$ is
  hydrogen,
  C$_{1-6}$ alkyl,
  aryl C$_{0-6}$ alkyl,
  carboxy C$_{0-6}$ alkyl,
  hydroxy C$_{0-6}$ alkyl,
  C$_{1-3}$ alkyloxy C$_{0-6}$ alkyl, or
  amino C$_{0-6}$ alkyl;
R$^7$ is
  hydrogen, fluorine
  C$_{1-8}$ alkyl,
  C$_{3-8}$ cycloalkyl,
  aryl C$_{0-6}$ alkyl,
  C$_{0-6}$ alkylamino C$_{0-6}$ alkyl,
  C$_{0-6}$ dialkylamino C$_{0-6}$ alkyl,
  C$_{1-8}$ alkylsulfonylamino C$_{0-6}$ alkyl,
  aryl C$_{0-6}$ alkylsulfonylamino C$_{0-6}$ alkyl,
  C$_{1-8}$ alkyloxycarbonylamino C$_{0-8}$-alkyl,
  aryl C$_{0-8}$ alkyloxycarbonylamino C$_{0-8}$ alkyl,
  C$_{1-8}$ alkylcarbonylamino C$_{0-6}$ alkyl,
  aryl C$_{0-6}$ alkylcarbonylamino C$_{0-6}$ alkyl,
  C$_{0-8}$ alkylaminocarbonylamino C$_{0-6}$ alkyl,
  aryl C$_{0-8}$ alkylaminocarbonylamino C$_{0-6}$ alkyl,
  C$_{1-6}$ alkylsulfonyl C$_{0-6}$ alkyl,
  aryl C$_{0-6}$ alkylsulfonyl C$_{0-6}$ alkyl,
  C$_{1-6}$ alkylcarbonyl C$_{0-6}$ alkyl
  aryl C$_{0-6}$ alkylcarbonyl C$_{0-6}$ alkyl,
  C$_{1-6}$ alkylthiocarbonylamino C$_{0-6}$ alkyl, or
  aryl C$_{0-6}$ alkylthiocarbonylamino C$_{0-6}$ alkyl wherein groups may be unsubstituted or substituted with one or more substituents selected from R$^1$ and R$^2$, and provided that when two R$^7$ groups are attached to the same carbon atom, they may be the same or different;
R$^8$ is
  hydroxy,
  C$_{1-6}$ alkyloxy,
  aryl C$_{1-4}$ alkyloxy, or
  C$_{1-6}$ alkylcarbonyloxy C$_{1-4}$ alkyloxy; and
R$^9$ is
  C$_{1-3}$ alkyl or -W-V, wherein W is C$_{1-3}$ alkyl and V is 6-membered monocyclic aromatic ring system containing 0, 1, 2, 3 or 4 heteroatoms selected from N, O and S.

A more preferred embodiment of the present invention is

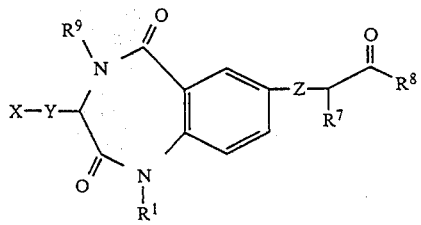

wherein:
X is
—NR$^1$R$^2$ or a 4- to 10-membered mono- or polycyclic aromatic or non-aromatic ring system containing 0, 1 or 2 heteroatoms chosen from N or O and either unsubstituted or substituted with R$^1$ and R$^2$, wherein R$^1$ and R$^2$ are independently chosen from:
  hydrogen,
  C$_{1-6}$ alkyl,
  aryl C$_{0-6}$ alkyl,
  carboxy C$_{0-6}$ alkyl,
  hydroxy C$_{0-6}$ alkyl,
  C$_{1-3}$ alkyloxy C$_{0-6}$ alkyl, or
  amino C$_{0-6}$ alkyl;
Y is
  C$_{0-6}$ alkyl,
  C$_{1-6}$ alkyl-CO-C$_{0-6}$ alkyl, or
  C$_{0-6}$ alkyl-NR$^3$-CO-C$_{0-6}$ alkyl wherein R$^3$ is hydrogen,
  C$_{1-6}$ alkyl,
  aryl C$_{0-6}$ alkyl,
  carboxy C$_{0-6}$ alkyl,
  hydroxy C$_{0-6}$ alkyl,
  C$_{1-3}$ alkyloxy C$_{0-6}$ alkyl, or
  amino C$_{0-6}$ alkyl;
Z is
  —(CH$_2$)$_m$—, or —C≡C—CH$_2$—;
  wherein m is 0–3;
R$^3$ is
  hydrogen,
  C$_{1-6}$ alkyl,
  aryl C$_{0-6}$ alkyl,
  carboxy C$_{0-6}$ alkyl,
  hydroxy C$_{0-6}$ alkyl,
  C$_{1-3}$ alkyloxy C$_{0-6}$ alkyl, or
  amino C$_{0-6}$ alkyl;
R$^7$ is
  hydrogen, fluorine C<sub>1-8</sub> alkyl,
C<sub>3-8</sub> cycloalkyl,
C<sub>0-6</sub> alkylamino C<sub>0-6</sub> alkyl,
C<sub>0-6</sub> dialkylamino C<sub>0-6</sub> alkyl,
C<sub>1-8</sub> alkylsulfonylamino C<sub>0-6</sub> alkyl, or
C<sub>1-8</sub> alkylcarbonylamino C<sub>0-6</sub> alkyl, wherein groups may be unsubstituted or substituted with one or more substituents selected from $R^1$ and $R^2$, and provided that when two $R^7$ groups are attached to the same carbon atom, they may be the same or different;

$R^8$ is
hydroxy,
C<sub>1-6</sub> alkyloxy,
aryl C<sub>1-4</sub> alkyloxy, or
C<sub>1-6</sub> alkylcarbonyloxy C<sub>1-4</sub> alkyloxy; and $R^9$ is
methyl or methylphenyl.

Especially preferred compounds of the invention are:

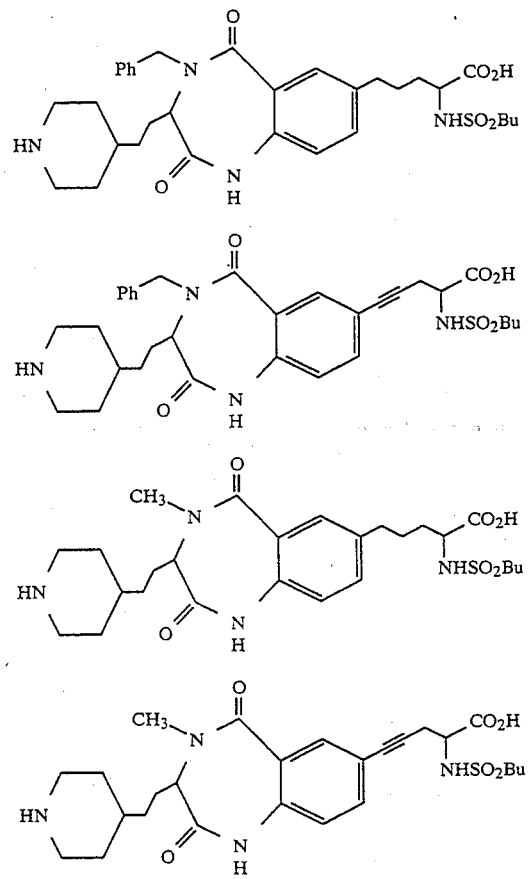

The portion of certain structures represented by "—≡—", which appears above and throughout the application, means "—C≡C—".

An ADP-stimulated platelet aggregation assay was used to determine inhibition associated with compounds of the invention.

Human platelets were isolated from fresh blood, collected into acid citrate/dextrose by differential centrifugation followed by gel filtration on Sepharose 2B in divalent ion-free Tyrode's buffer (pH 7.4) containing 2% bovine serum albumin. Platelet aggregation was measured at 37° C. in a Chronolog aggregometer. The reaction mixture contained gel-filtered human platelets ($2 \times 10^8$ per ml), fibrinogen (100 μg/ml), $Ca^{2+}$ (1 mM), and the compound to be tested. Aggregation was initiated by adding 10 uM ADP 1 minute after the other components had been added. The reaction was allowed to proceed for at least 2 minutes. The extent of inhibition of aggregation was expressed as the percentage of the rate of aggregation observed in the absence of inhibitor. The $IC_{50}$ is the dose of a particular compound inhibiting aggregation by 50% relative to a control lacking the compound.

The abbreviations listed below are defined as Bn, benzyl; NMM, N-methylmorpholine; HOBt, 1-hydroxybenzotriazole; EDC, 1-(3-dimethylaminopropyl)-3-ethylcarbodiimide hydrochloride; DMF, dimethylformamide; Pib, 4-(4-piperidyl)butanoyl; pTSA, paratoluenesulfonic acid; DMS, dimethylsulfide; TFA, trifluoroacetic acid; THF, tetrahydrofuran; DIBAL, diisobutylaluminumhydride; Boc (or BOC), tert-butoxycarbonyl; Cbz, benzyloxycarbonyl; Suc, succinoyl; alpine borane, β-isopinocamphenyl-9-borabicyclo[3.3.1]-nonane; TBDMS, tertbutyldimethylsilyl; Jones reagent, chromic acid; NBS, N-Bromosuccinimide; BPO, Benzoyl peroxide; PPh<sub>3</sub>, triphenyl phosphine; DMSO, Dimethylsulfoxide; Et<sub>3</sub>N, triethylamine; Tf<sub>2</sub>O, triflicanhydride; DMAP, 4-dimethylaminopyridine; BOP, benzotriazol-1 yloxytris(dimethylamino)-phosphonium hexafluorophosphate; PhCHO, benzaldehyde; and Boc<sub>2</sub>O, di-t-butyldicarbonate; dppp, 1,3bis(diphenylphosphino)propane; ETOH, ethyl acetate; CH<sub>2</sub>Cl<sub>2</sub>, methylene chloride; HOAc, acetic acid; CH<sub>3</sub>OH, methanol; CHCl<sub>3</sub>, chloroform.

Unless otherwise indicated, all degree values are Celsius.

The pharmaceutically acceptable salts of the compounds of Formula I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylene-diamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., *Amer. J. Physiol.*, 1987,252:H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration occurs subsequent to angioplasty, and is in an amount sufficient to inhibit platelet aggregation, e.g. an amount which achieves a steady state plasma concentration of between about 0.01–50 mM preferably between about 0.01–10 mM.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carders or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amounts of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The compounds of Formula I are prepared according to the reaction schemes set forth below.

EXAMPLE 1

Preparation of Boc-4-Piperidine-2-ethanol (1-5)

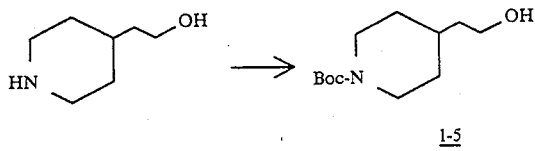

4-Piperidine-2-ethanol (Aldrich) (130 g, 1.0 mole) was dissolved in 700 mL dioxane, cooled to 0° C. and treated with 3N NaOH (336 mL, 1.0 mole), and di-t-butyldicarbonate (221.8 g, 1.0 mole). The ice bath was removed and the reaction stirred overnight. The reaction was concentrated, diluted with water and extracted with ether. The ether layers were combined, washed with brine, dried over MgSO$_4$, filtered and evaporated to give 1-5 R$_f$=0.37 in 1:1 EtOAc/Hexanes, ninhydrin stain.

$^1$H NMR (300MHz, CDCl$_3$) δ4.07 (bs, 2H), 3.7 (bs, 2H), 2.7 (t, J=12.5 Hz, 2H), 1.8–1.6 (m, 6H), 1.51 (s, 9H), 1.1 (ddd, J=4.3, 12.5, 12 Hz, 2H).

Boc-4-piperidine-2-ethyl iodide (1-6)

Boc-4-piperidine-2-ethanol (1-5) (10.42 g, 0.048 mole was dissolved in 400 ml benzene and imidazole (4.66 g, 0.068 moles) and triphenylphosphine (15.24 g, 0.05 moles) were added at room temperature. After 6 hours the reaction mixture was filtered and the filtrate was evaporated to give a dark residue. This was purified by flash chromatography on silica gel eluting with 10% EtOAc-hexanes to give 1-6 as a yellow oil.

EXAMPLE 2

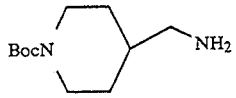

4-(N-t-Butyloxycarbonylpiperidinyl)methylamine (2-3)

A solution of 4-(piperidinyl)methylamine (22.8 g, 0.2 mmoles) in toluene (250 ml) was treated with benzaldehyde (21.2 g, 0.2 mmoles) at room temperature and the resulting mixture was heated at reflux for 3 hours with the aid of a Dean-Stark trap for water removal. The cooled reaction mixture containing the desired Schiff's base was treated portionwise with di-t-butyl dicarbonate (47.96 g, 0.22 moles) and the resulting solution was stirred at room temperature for 16 hours. The solvent was then removed and the residue was cooled to 0–5° C. and treated with 1N KHSO$_4$ (220 ml) with stirring for 3 hours. The resulting reaction mixture was extracted with ether (3×200 ml) and then made basic with 1N KOH solution and extracted with CHCl$_3$ (4×75 ml). The combined organic extract was washed with brine, dried (Na$_2$SO$_4$) filtered through celite, and the solvent removed to provide pure 2-3 as a clear oil.

$^1$H NMR (300 MHz, CDCl$_3$)δ1.13 (2H, m), 1.45 (9H, s), 1.60 (1H, m), 1.74 (2H, d), 2.68 (4H, m), 4.15 (2H, bd).

EXAMPLE 3

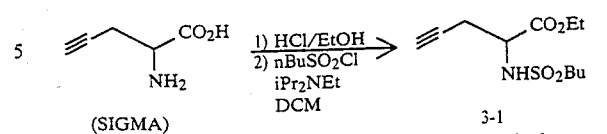

2-(Butanesulfonylamino)pent-4-ynoic acid, ethyl ester (3-1)

A solution of propargylglycine ethyl ester hydrochloride (from treatment of 2.0g (17.7mmol) of propargylglycine with EtOH/HCl at reflux) in CH$_2$Cl$_2$ (30 ml) and 10ml (57mmol) diisopropylethylamine was cooled to 0° C. and 35ml of butanesulfonyl chloride added dropwise. After 30 minutes, the reaction mixture was poured into cold 10% citric acid solution and extracted with ether. The organic phase was washed with NaHCO$_3$ solution, brine and dried (MgSO$_4$). The crude product was purified by flash colunto chromatography to afford 2.6g of 3-1.

NMR (300 MHz, CDCl$_3$): 5.12 (d, 1H), 4.27 (m, 3H), 3.06 (m, 2H), 2.68 (m, 2H), 2.09 (t, 1H), 1.83 (m, 2H), 1.45 (m, 2H), 1.31 (t, 3H), 0.95 (t, 1H).

EXAMPLE 4

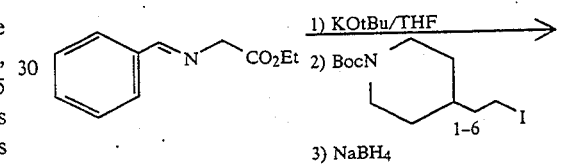

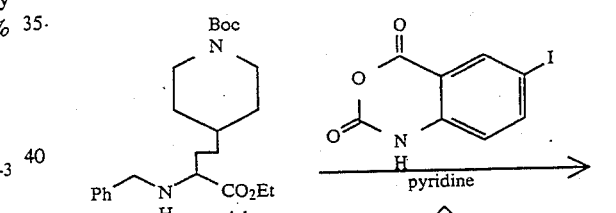

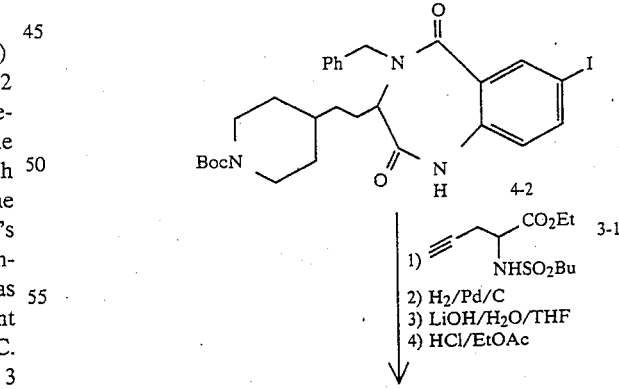

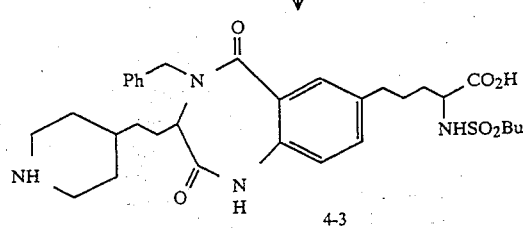

-continued

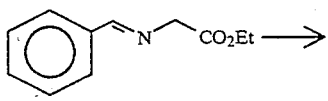

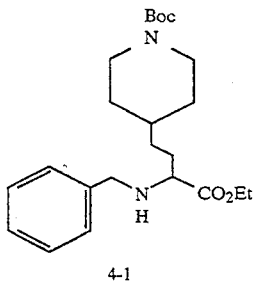

4-1

N-Benzyl-2-[(N-Boc-piperidin-4-yl)ethyl]-glycine, ethyl ester (4-1)

A solution of glycine benzaldehyde imine (10.2 g, 53 mmol) in 100 ml of THF was added dropwise to a cooled (−78° C.) and stirred solution of potassium t-butoxide (5.8 g, 52 mmol) in 300 ml THF over 20 min. After 15 min. a solution of Boc-4-(2-iodoethyl) piperidine (1-6) (18.2 g, 52 mmol) was added and stirring continued at −78° C. for 2 h. followed by standing at −20° C. for 18 h. After stirring 2 h. at r.t., the reaction mixture was concentrated to 50% of volume, poured into ice cold saturated NH4Cl and extracted with ether. The organic phase was washed with brine, dried (MgSO4) and the solvent evaporated. 1 g of the resulting oil was dissolved in 10 ml of methanol, cooled to 0° C. and 100 mg of sodium borohydride added in portions over 5 mins. After an additional 10 min., the reaction was concentrated, poured into water and extracted with ether. The organic extracts were washed with brine, dried (MgSO4) and solvent evaporated to give crude product purified by flash column chromatography (5:1→2:1 hexane:EtOAc) to afford 410 mg of 4-1.

NMR (300 MHz, CDCl3)δ7.2–7.4 (m, 5H), 4.17 (q, 2H), 4.05 (brs, 2H), 3.80 (d, ½ of AB, 1H), 3 and 2 (d, ½ of AB, 1H), 3.22 (t, 1H), 2.63 (brt, 2H), 0.95–1.9 (m, 22H).

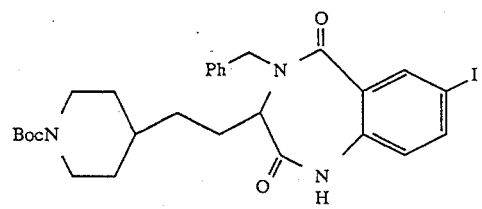

7-Iodo-4-benzyl-3-[2-(N-Boc-piperidin-4-yl)ethyl]- 1 H-1,4dioxobenzodiazipine (4-2)

A mixture of 4-iodoisatoic anhydride (3.5 g, 12.1 mmol) (Ann. Chim. (Rome) vol. 57, no. 6 (1967) pp. 607-615) and amino ester 4-1 (5.0 g, 12-3 mmol) in 35 ml of pyridine was heated to reflux for 40 h. The solvent was evaporated and the residue purified by flash chromatography (EtOAc→20% EtOH/EtOAc) to afford 4.0 g of 4-2 as a foam.

NMR (300 MHz, CD3OD) 8.4 (brs, 1H), 7.85 (d, 1H), 6.95–7.5 (m, 6H), 4.45–4.8 (m, 2H), 3.9–4.3 (m, 3H), 2.6 (brs, 2H), 0.7–2.0 (m, 18H).

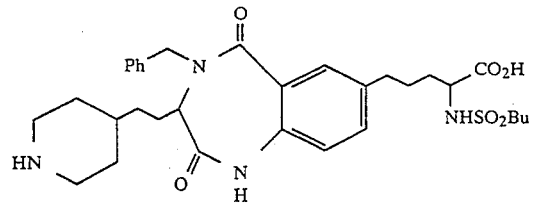

2-Butanesulfonylamino-5-[4-benzyl-3-(2-[piperidin-4-yl]ethyl- 1 H- 1,4-dioxobenzodiazepin-7-yl]pentanoic acid, trifluoroacetate salt (4-3)

A mixture of iodide (975 mg, 1.61 mmol), acetylene (3-1), (500 mg, 1.91 mmol), bis(triphenylphosphine) palladium (II) chloride (80 mg, 0.11 mmol) and copper (I) iodide (40 mg, 0.21 mmol) in diethylamine (12 ml) was stirred in the dark at room temperature for 3 hours, under argon. The volatiles were evaporated and the residue partitioned between 10% citric acid solution and ethyl acetate. The organic phase was washed with water, saturated NaHCO3, brine and dried (MgSO4). The solvent was evaporated to give 930 mg of a yellow foam.

150 mg of this was dissolved in 25 ml of EtOAc and hydrogenated at 50 psi over 10% palladium charcoal, for 18 hours to give, after filtration and evaporation, 150 mg of a gum. This was dissolved in THF (3 ml) and 1M NaOH (3 ml) aded, followed by 1 ml methanol. The reaction mixture was stirred for 18 hours, concentrated and partitioned between EtOAc and water. The organic phase was washed with water and brine, dried (MgSO4) and the solvent evaporated to give a foam which partially dissolved in 3 ml of CH2Cl2. After cooling to −10° C., trifluoroacetic acid (3 ml) was added and stirring continued for 15 minutes before evaporation of volatiles. The resulting gum was purified by reverse phase preparative HPLC to give 4-3. M.S. (POS FAB) 657 (M+ +CO2+1).

NMR (300 MHz), 8.0 (d, 1H), 7.57 (d, 1H), 7.2–7.46 (m, 6H), 4.1–4.7 (m, 3H), 4.02 (dd, 1H), 3.02 (t, 2H), 2.7–2.95 (m, 4H), 1.65–2.0 (m, 10H), 1.1–1.5 (m, 7H), 0.94 (t, 3H).

EXAMPLE 5

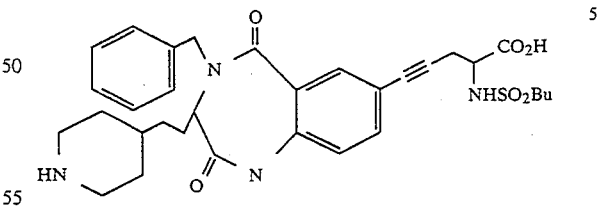

2-Butanesulfonylamino-5-[4-benzyl-3-(2-[piperidin-4-yl]ethyl-1H.-1,4-dioxobenzodiazepin-7-yl]pent-4-ynoic acid, trifluoroacetate salt (5)

Iodide 4-2 was coupled with acetylene 3-1 and deprotected as described in 4-3 to provide 5. M.S. (POS FAB) 653M+ +CO2+1.

| | C | H | N |
|---|---|---|---|
| Analysis calculated for 1.8 CF3CO2H | 52.53 | 5.18 | 6.88 |
| Obs | 52.58 | 5.14 | 6.81 |

EXAMPLE 6

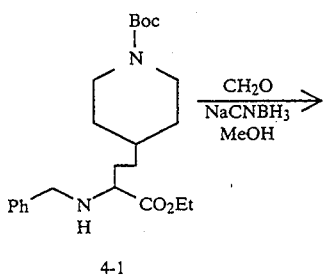

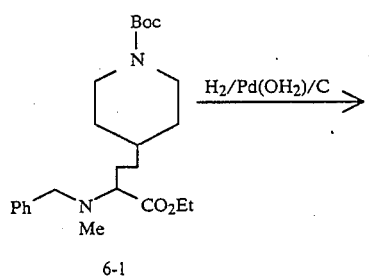

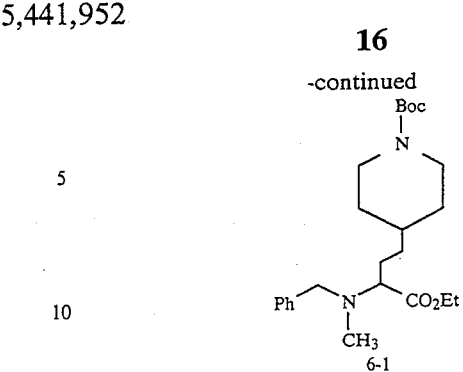

N-Benzyl-N-Methyl-[2-(N-Boc-piperidin-4-yl)ethyl]glycine, ethyl ester (6-1)

Amine 4-1 (1.3 g, 3.2 mmol) was dissolved in 25 ml of methanol and 37% formaldehyde solution (0.3 mL) added, followed by 300 mg of sodium cyanoborohydride. The reaction mixture was stirred at r.t. overnight, poured into water and extracted with water and brine, dried (MgSO$_4$) and the solvent evaporated to give 6-1.

NMR (300 MHz, CDCl$_2$) 7.2–7.35 (m, 5H), 3.9–4.3 (m, 4H), 3.78 (½ of AB 1H), 3.57 (½ of AB 1H), 3.23 (t, 2H), 2.63 (brt, 2H), 2.26 (3 s, 3H), 1.6–1.8 (m, 5H), 1.44 (s, 9H), 1.31 (t, 3H), 1.0–1.4 (m, 4H).

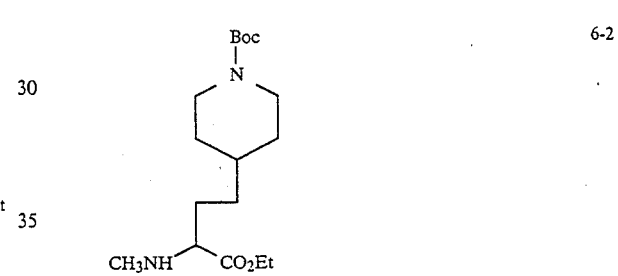

N-Benzyl-[2-(N-Boc-piperidin-4-yl)ethyl]glycine, ethyl ester (6-2)

A solution of amine 6-1 (1.2 g, 2.87 mmol) in 50 ml EtOH was hydrogenated at 50 psi over 100 mg of 10% palladium hydroxide on charcoal for 18 h. The catalyst was removed by filtration and the filtrate evaporated to give methylamine 6-2.

NMR (300 MHz, CDCl$_3$) δ4.19 (q, 2H), 4.04 (brs, 2H), 3.1 (t, 1H), 2.69 (brt, 2H), 2.37 (s, 3H), 1.0–1.7 (m, 21H).

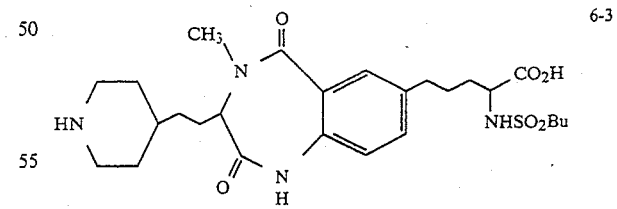

2-Butanesulfonylamino-5-[4-methyl-3-(2-piperidin-4-yl)ethyl]- 1 H, 1,4-dioxobenzodiazepin-7-yl]pentanoic acid, trifluoroacetate salt (6-3)

Using the same procedure as described for the preparation of but replacing benzylamine 4-1 with methylamine 6-2 afforded 6-3. (saturated)

NMR (300 MHz, D$_2$O)δ7.76, (d, 1H), 7.40 (d, 1H), 7.23 (m, 1H), 4.22 (m, 1H), 3.82 (m, 1H), 3.22 (brd, 2H), 2.95 (t, 2H), 2.83 (s, 3H), 2.76 (m, 2H), 2.56 (m, 2H), 1.0–2.0 (m, 17H), 0.67 (t, 3H).

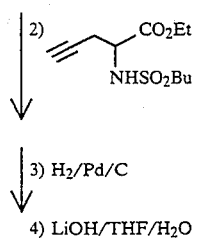

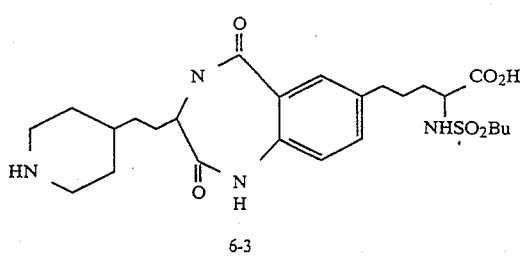

EXAMPLE 7

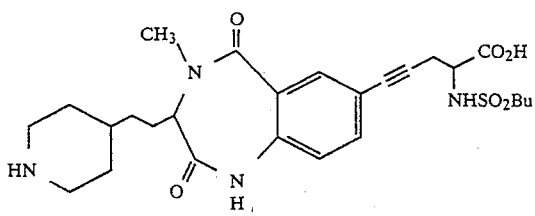

2-Butanesulfonylamino-5-[4-methyl-3-[2-[piperidin-4-yl]ethyl]- 1 H- 1,4-dioxobenzodiazepin-7-yl]pent-4-ynoic acid, trifluoroacetate salt (7)

Utilizing the same scheme described for preparation of 5, but using methylamine 6-2 in place of benzylenene 4-1, afforded acetylene 7.

NMR (300 MHz, $D_2O$) δ 7.93 (brs, 1H), 7.58 (d, 1H), 7.20 (m, 1H), 4.23 (brs, 1H), 4.16 (dd, 1H), 3.94 (q, 1H), 3.23 (brd, 2H), 3.04 (m, 2H), 2.6–2.9 (m, 8H), 0.95–2 (m, 17H), 0.59 (t, 3H).

What is claimed is:

1. A fibrinogen receptor antagonist of the following formula:

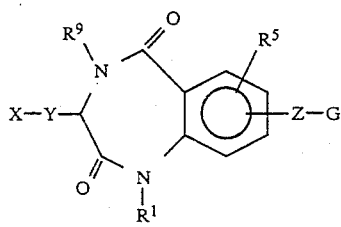

wherein G is

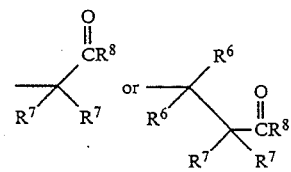

X is
  3-piperidinyl;
Y is
  $C_{1-8}$ alkylene;
Z is
  $-(CH_2)_m-$, $-C\equiv C-CH_2-$

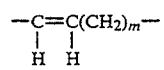

wherein m is 0–6;
$R^5$ is
  hydrogen
  $C_{1-6}$ alkyl,
  $C_{0-6}$ alkylcarboxy $C_{0-6}$ alkyl,
  $C_{0-6}$ alkyloxy $C_{0-6}$ alkyl,
  hydroxy $C_{0-6}$ alkyl,
  aryl $C_{0-6}$ alkyl, or
  halogen;
$R^6$ is
  hydrogen,
  $C_{1-8}$ alkyl,
  aryl $C_{0-6}$ alkyl,
  $C_{3-8}$ cycloalkyl $C_{0-6}$ alkyl,
  $C_{0-6}$ alkylcarboxy $C_{0-6}$ alkyl, carboxy $C_{0-6}$ alkyl,
  $C_{1-4}$ alkyloxy $C_{0-6}$ alkyl, or
  hydroxy $C_{0-6}$ alkyl, provided that any of which groups may be substituted or unsubstituted independently with $R^1$ or $R^2$, and provided that, when two $R^6$ groups are attached to the same carbon, they may be the same or different;
$R^7$ is
  hydrogen, fluorine
  $C_{1-8}$ alkyl,
  $C_{3-8}$ cycloalkyl,
  aryl $C_{0-6}$ alkyl,
  $C_{0-6}$ alkylamino $C_{0-6}$ alkyl,
  $C_{0-6}$ dialkylamino $C_{0-6}$ alkyl,
  $C_{1-8}$ alkylsulfonylamino $C_{0-6}$ alkyl,
  aryl $C_{0-6}$ alkylsulfonylamino $C_{0-6}$ alkyl,
  $C_{1-8}$ alkyloxycarbonylamino $C_{0-8}$ -alkyl,
  aryl $C_{0-8}$ alkyloxycarbonylamino $C_{0-8}$ alkyl,
  $C_{1-8}$ alkylcarbonylamino $C_{0-6}$ alkyl,
  aryl $C_{0-6}$ alkylcarbonylamino $C_{0-6}$ alkyl,
  $C_{0-8}$ alkylaminocarbonylamino $C_{0-6}$ alkyl,
  aryl $C_{0-8}$ alkylaminocarbonylamino $C_{0-6}$ alkyl,
  $C_{1-6}$ alkylsulfonyl $C_{0-6}$ alkyl,
  aryl $C_{0-6}$ alkylsulfonyl $C_{0-6}$ alkyl,
  $C_{1-6}$ alkylcarbonyl $C_{0-6}$ alkyl
  aryl $C_{0-6}$ alkylcarbonyl $C_{0-6}$ alkyl,
  $C_{1-6}$ alkylthiocarbonylamino $C_{0-6}$ alkyl, or
  aryl $C_{0-6}$ alkylthiocarbonylamino $C_{0-6}$ alkyl
    wherein groups may be unsubstituted or substituted with one or more substituents selected from $R^1$ and $R^2$, and provided that when two $R^7$ groups are attached to the same carbon atom, they may be the same or different;
$R^8$ is
  hydroxy,
  $C_{1-8}$ alkyloxy,
  aryl $C_{0-6}$ alkyloxy,
  $C_{1-8}$ alkylcarbonyloxy $C_{1-4}$ alkyloxy,
  aryl $C_{1-8}$ alkylcarbonyloxy $C_{1-4}$ alkyloxy, or
  an L- or D-amino acid joined by an amide linkage and wherein the carboxylic acid moiety of said amino acid is as the free acid or is esterified by $C_{1-6}$ alkyl; and
R9 is
  hydrogen, $C_{1-8}$ alkyl,; phenyl or phenyl $C_{1-3}$ alkyl.

2. A compound of claim 1, having the formula

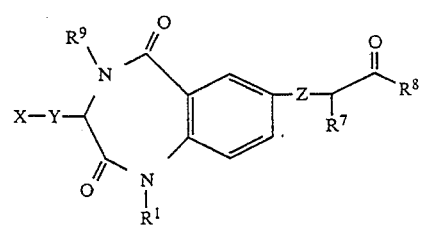

wherein:
X is
  3-piperidinyl;
Y is
  $C_{1-8}$ alkylene;
Z is
  $-(CH_2)_m-$, or $-C\equiv C-CH_2-$;
  wherein m is 0–6;

R³ is
  hydrogen,
  C₁₋₆ alkyl,
  aryl C₀₋₆ alkyl,
  carboxy C₀₋₆ alkyl,
  hydroxy C₀₋₆ alkyl,
  C₁₋₃ alkyloxy C₀₋₆ alkyl, or
  amino C₀₋₆ alkyl;
R⁷ is
  hydrogen, fluorine
  C₁₋₈ alkyl,
  C₃₋₈ cycloalkyl,
  aryl C₀₋₆ alkyl,
  C₀₋₆ alkylamino C₀₋₆ alkyl,
  C₀₋₆ dialkylamino C₀₋₆ alkyl,
  C₁₋₈ alkylsulfonylamino C₀₋₆ alkyl,
  aryl C₀₋₆ alkylsulfonylamino C₀₋₆ alkyl,
  C₁₋₈ alkyloxycarbonylamino C₀₋₈ alkyl,
  aryl C₀₋₈ alkyloxycarbonylamino C₀₋₈ alkyl,
  C₁₋₈ alkylcarbonylamino C₀₋₆ alkyl,
  aryl C₀₋₆ alkylcarbonylamino C₀₋₆ alkyl,
  C₀₋₈ alkylaminocarbonylamino C₀₋₆ alkyl,
  aryl C₀₋₈ alkylaminocarbonylamino C₀₋₆ alkyl,
  C₁₋₆ alkylsulfonyl C₀₋₆ alkyl,
  aryl C₀₋₆ alkylsulfonyl C₀₋₆ alkyl,
  C₁₋₆ alkylcarbonyl C₀₋₆ alkyl
  aryl C₀₋₆ alkylcarbonyl C₀₋₆ alkyl,
  C₁₋₆ alkylthiocarbonylamino C₀₋₆ alkyl, or
  aryl C₀₋₆ alkylthiocarbonylamino C₀₋₆ alkyl
    wherein groups may be unsubstituted or substituted with one or more substituents selected from R¹ and R², and provided that when two R⁷ groups are attached to the same carbon atom, they may be the same or different;
R⁸ is
  hydroxy,
  C₁₋₆ alkyloxy,
  aryl C₁₋₄ alkyloxy, or
  C₁₋₆ alkylcarbonyloxy C₁₋₄ alkyloxy; and
R⁹ is
  C₁₋₃ alkyl phenyl or phenyl C₁₋₃ alkyl, 3. A compound of claim 2, having the formula:

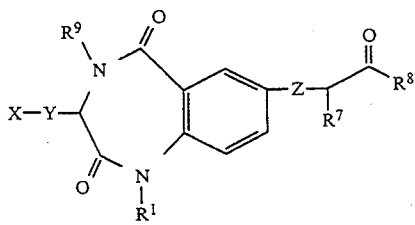

II wherein:
X is
  3-piperidinyl;
Y is
  C₁₋₈ alkylene;
Z is
  —(CH₂)ₘ—, or —C≡C—CH₂—;
  wherein m is 0–3;
R³ is
  hydrogen,
  C₁₋₆ alkyl,
  aryl C₀₋₆ alkyl,
  carboxy C₀₋₆ alkyl,
  hydroxy C₀₋₆ alkyl,
  C₁₋₃ alkyloxy C₀₋₆ alkyl, or
  amino C₀₋₆ alkyl;
R⁷ is
  hydrogen, fluorine
  C₁₋₈ alkyl,
  C₃₋₈ cycloalkyl,
  C₀₋₆ alkylamino C₀₋₆ alkyl,
  C₀₋₆ dialkylamino C₀₋₆ alkyl,
  C₁₋₈ alkylsulfonylamino C₀₋₆ alkyl, or
  C₁₋₈ alkylcarbonylamino C₀₋₆ alkyl;
  wherein groups may be unsubstituted or substituted with one or more substituents selected from R¹ and R², and provided that when two R⁷ groups are attached to the same carbon atom, they may be the same or different;
R⁸ is
  hydroxy,
  C₁₋₆ alkyloxy,
  aryl C₁₋₄ alkyloxy, or
  C₁₋₆ alkylcarbonyloxy C₁₋₄ alkyloxy; and
R⁹ is
  methyl or phenylmethyl.

4. A compound of claim 3 selected from the group of

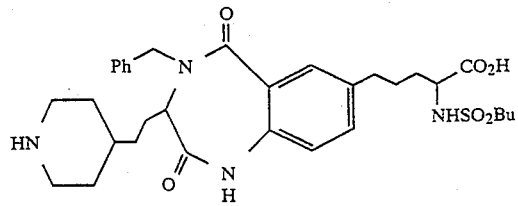

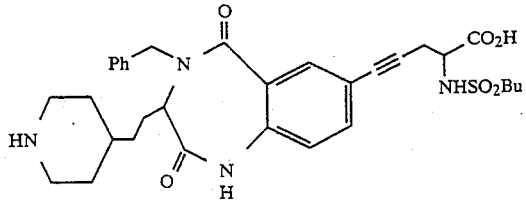

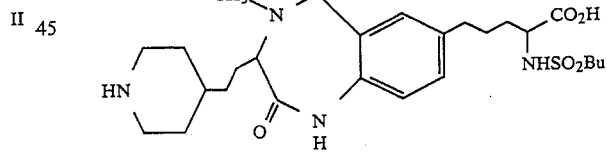

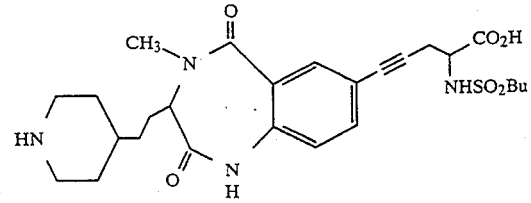

5. A compound of claim 1 for use in inhibiting the binding of fibrinogen to blood platelets, inhibiting the aggregation of blood platelets, treating thrombus formation or embolus formation, or preventing thrombus or embolus formation in a mammal.

6. A composition for inhibiting the binding of fibrinogen to blood platelets in a mammal, comprising a compound of claim 1 and a pharmaceutically acceptable carrier.

7. A composition for inhibiting the aggregation of blood platelets in a mammal, comprising a compound of claim 1 and a pharmaceutically acceptable carder.

8. A composition for preventing thrombus or embolus formation in a mammal, comprising a compound of claim 1 and a pharmaceutically acceptable carder.

9. A composition for treating thrombus or embolus formation in a mammal, comprising a compound of claim 1 and a pharmaceutically acceptable carder.

10. A method for inhibiting the binding of fibrinogen to blood platelets in a mammal, comprising administering to the mammal a composition of claim 7.

11. A method for inhibiting the aggregation of blood platelets in a mammal, comprising administering to the mammal the composition of claim 7.

12. A method for preventing thrombus or embolus formation in a mammal, comprising administering to the mammal the composition of claim 8.

13. A method for treating thrombus or embolus formation in a mammal, comprising administering to the mammal the composition of claim 9.

14. A compound of claim 4 for use in inhibiting the binding of fibrinogen to blood platelets, inhibiting the aggregation of blood platelets, treating thrombus formation or embolus formation, or preventing thrombus or embolus formation in a mammal.

15. A composition for inhibiting the binding of fibrinogen to blood platelets in a mammal, comprising a compound of claim 4 and a pharmaceutically acceptable carder.

16. A composition for inhibiting the aggregation of blood platelets in a mammal, comprising a compound of claim 4 and a pharmaceutically acceptable carder.

17. A composition for preventing thrombus or embolus formation in a mammal, comprising a compound of claim 4 and a pharmaceutically acceptable carder.

18. A composition for treating thrombus or embolus formation in a mammal, comprising a compound of claim 4 and a pharmaceutically acceptable carder.

19. A method for inhibiting the binding of fibrinogen to blood platelets in a mammal, comprising administering to the mammal a composition of claim 15.

20. A method for inhibiting the aggregation of blood platelets in a mammal, comprising administering to the mammal the composition of claim 16.

21. A method for preventing thrombus or embolus formation in a mammal, comprising administering to the mammal the composition of claim 17.

22. A method for treating thrombus or embolus formation in a mammal, comprising administering to the mammal the composition of claim 18.

* * * * *

UNITED STATES PATENT AND TRADEMARK OFFICE
CERTIFICATE OF CORRECTION

PATENT NO. : 5,441,952

DATED : August 15, 1995

INVENTOR(S) : Claremon, et al

It is certified that error appears in the above-identified patent and that said Letters Patent is hereby corrected as shown below:

In Claim 1, column 17, line 47, delete "3-piperidinyl" and insert --4-piperidinyl--.

In Claim 2, column 18, line 63, delete "3-piperidinyl" and insert --4-piperidinyl--.

In Claim 3, column 19, line 56, delete "3-piperidinyl" and insert --4-piperidinyl--.

Signed and Sealed this

Twelfth Day of March, 1996

BRUCE LEHMAN

*Attest:*

*Attesting Officer*     Commissioner of Patents and Trademarks